United States Patent
Abou Nader et al.

(10) Patent No.: US 8,738,399 B1
(45) Date of Patent: May 27, 2014

(54) METHODS AND SYSTEMS FOR DRUG PURCHASE VALIDATION

(75) Inventors: Jo-Ellen Abou Nader, Chesterfield, MO (US); Suzanne B. Mitchell, Belleville, IL (US)

(73) Assignee: Express Scripts, Inc., St. Louis, MO (US)

( * ) Notice: Subject to any disclaimer, the term of this patent is extended or adjusted under 35 U.S.C. 154(b) by 8 days.

(21) Appl. No.: 13/340,809

(22) Filed: Dec. 30, 2011

(51) Int. Cl.
*G06Q 50/22* (2012.01)

(52) U.S. Cl.
USPC .................................................. 705/2

(58) Field of Classification Search
CPC ...... G06Q 50/22; G06Q 50/24; G06F 19/238; G06F 19/322; G06F 19/3456
See application file for complete search history.

(56) References Cited

U.S. PATENT DOCUMENTS

| | | | |
|---|---|---|---|
| 7,917,372 | B2 | 3/2011 | Oscar et al. |
| 2004/0006490 | A1 | 1/2004 | Gingrich et al. |
| 2006/0085230 | A1 | 4/2006 | Brill et al. |
| 2006/0217824 | A1 | 9/2006 | Allmon et al. |
| 2007/0011030 | A1 * | 1/2007 | Bregante et al. ............... 705/4 |
| 2011/0257991 | A1 * | 10/2011 | Shukla ........................... 705/2 |
| 2011/0288886 | A1 * | 11/2011 | Whiddon et al. ............... 705/3 |

OTHER PUBLICATIONS

AuditTrack, Desk Audit, ACS Audit & Compliance Solutions, A Xerox Company, 2010.
AudiTrack© Automated Healthcare Review System, ACS Audit & Compliance Solutions, A Xerox Company, retrieved on Jun. 21, 2011.
Caremark Standard Audit Practice, Jan. 2009.
Pharmacy Audits. Who's Watching the Store?, ScripNet, www.scripnet.com/news/2010/07/pharmacy-audits-whos-watching-the-store/, retrieved on Jun. 21, 2011.
Pharmacy Claims Auditing, CGI Group, Inc., www.cgi.com/usfederal, Jun. 2010.

* cited by examiner

*Primary Examiner* — Elaine Gort
*Assistant Examiner* — Gregory Lultschik
(74) *Attorney, Agent, or Firm* — Husch Blackwell LLP (57) ABSTRACT

In an example embodiment, drug sale data is accessed from a prescription drug wholesaler regarding prescription drugs sold to the pharmacy by the prescription drug wholesaler during a period of time. Pharmacy claims data over the period of time is accessed, where the pharmacy claims data reflects a plurality of claims that were submitted for adjudication by the pharmacy during the period of time. A number of units of a prescription drug associated with the plurality of claims submitted during the period of time by the pharmacy for adjudication are determined based on the pharmacy claims data. This number of units of the prescription drug is compared with the number of units of the prescription drug sold to the pharmacy. A determination is then made as to whether a discrepancy exists based on the results of the comparison. Additional methods and systems are disclosed.

22 Claims, 9 Drawing Sheets

METHODS AND SYSTEMS FOR DRUG PURCHASE VALIDATION

FIELD

The field relates to fraud detection, and more particularly to electronic verification of prescription drug sales by a pharmacy.

BACKGROUND

Pharmacy benefit managers (PBMs) offer prescription drug benefit plans that allow members to have drug prescriptions filled at various in-network pharmacy locations. These locations may include retail locations, mail locations, or both retail and mail locations.

When a physician writes a prescription for a patient, the patient takes the prescription to a pharmacy to have the prescription filled. The pharmacy submits the prescription to the PBM for adjudication, fills the prescription, and accepts a co-pay from the patient. Once the PBM adjudicates the matter, it reimburses the pharmacy a predetermined amount for the specific drug sold to the patient. The pharmacy then purchases additional doses of the drug prescribed to the patient from a drug wholesaler in order to refill its stock.

DETAILED DESCRIPTION

The purchase verification system and method may protect against the proliferation of prescription drugs, such as the addictive class C-2 narcotics, and may help to prevent the fraudulent submission of prescription claims for adjudication by a PBM. The purchase verification system and method monitors the quantity of prescription drugs distributed to a pharmacy and the quantity of prescription drugs reportedly dispensed by the pharmacy, and determines whether there are any discrepancies which would indicate that the pharmacy has submitted claims to the PBM for more doses of a given drug than the pharmacy has purchased.

A discrepancy is detected by the purchase validation device which accesses information relating to drugs sold to a pharmacy, as well as information regarding claims submitted for adjudication by the pharmacy to a PBM. The purchase validation device determines therefrom data regarding units of a prescription drug, which may include the number and type of drugs purchased by the pharmacy and/or reportedly dispensed by the pharmacy. By analyzing this data, the purchase validation device may determine that a pharmacy has reportedly filled prescriptions for more drugs than it has purchased, which may indicate fraud.

Figure 1:
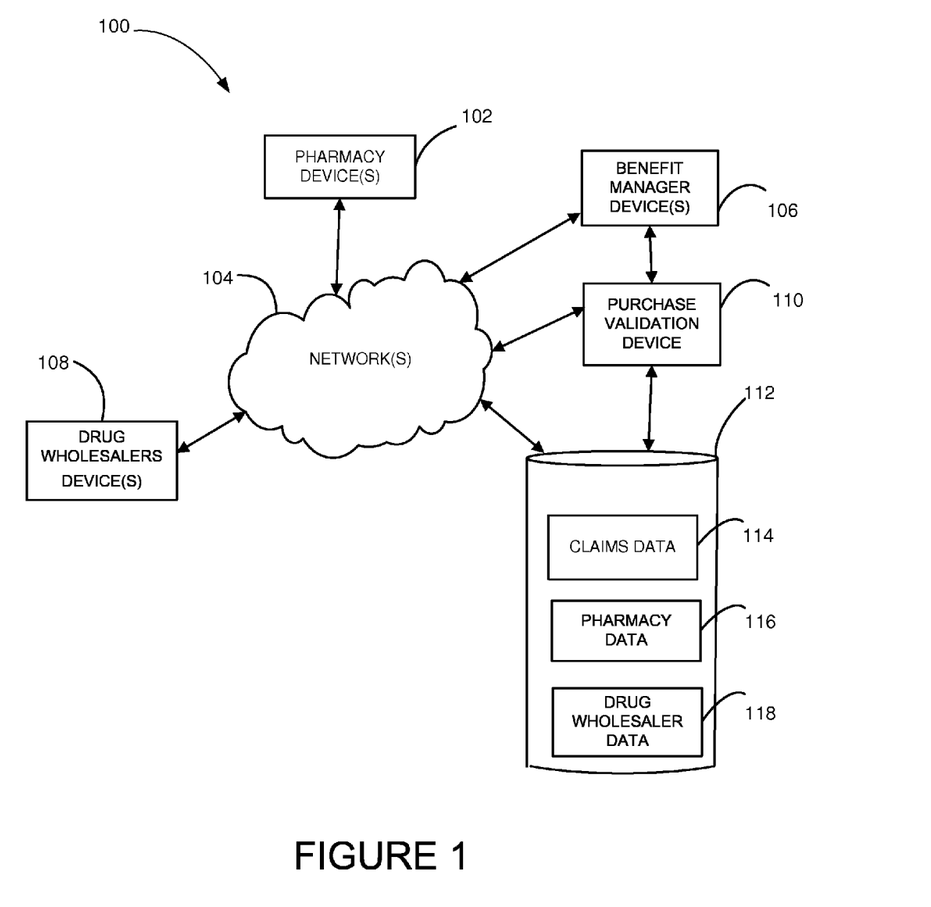
FIG. 1 is a block diagram of an example network of a pharmacy, a drug wholesaler and a PBM, according to an example embodiment.

FIG. 1 illustrates a block diagram of an example system, as described above, according to an example embodiment. The system 100 is an example environment in which the claims associated with a pharmacy may be verified. The system 100, as shown in FIG. 1, includes a pharmacy device 102, a benefit manager device 106, a drug wholesale device 108, and a purchase validation device 110.

The pharmacy device 102 may be in communication with a benefit manager device 106 over a network 104. The pharmacy device 102 may be operated by a pharmacy (which may be a retail pharmacy, a mail order pharmacy, a specialty pharmacy, or the like), or an entity that is at least partially responsible for submitting prescription claims to a PBM.

The network 104 by which the pharmacy device 102 communicates with the benefit manager device 106 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Network 104 may also include optical or wired communications. Other conventional and/or later developed wired and wireless networks may also be used.

The benefit manager device 106 is a device operated by an entity at least partially responsible for creation and/or management of the pharmacy benefit. While the benefit manager operating the benefit manager device 106 is typically a PBM, other entities may operate the benefit manager device 106 either on behalf of themselves, the PBM, or another entity.

Some of the operations of the PBM that operates the benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of the client with the PBM. The member's co-pay may be based on be a flat co-pay (e.g., $10), co-insurance (e.g., 10%), and/or a deductible (e.g., for first $500 of annual prescription drug spend) for certain prescription drugs, certain types of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug.

In conjunction with receiving the co-pay (if any) from the member and dispensing the prescription drug to the member, the pharmacy submits a claim to the PBM for the prescription drug. The PBM may perform certain adjudication functions including verifying the eligibility of the member, reviewing the formulary to determine appropriate co-pay, coinsurance, and deductible for the prescription drug, and performing a drug utilization review (DUR) on the member. The PBM then adjudicates the claim associated with the prescription drug and provides a response to the pharmacy following performance of the aforementioned functions. As part of the adjudication, the client (or the PBM on behalf of the client) ultimately reimburses the pharmacy for filling the prescription drug when the prescription drug was successfully adjudicated. The aforementioned adjudication functions generally occur before the co-pay is received and the prescription drug dispensed. However, the operations may occur simultaneously, substantially simultaneously, or in a different order. In addition, more or less adjudication functions may be performed as part of the adjudication process.

The amount of reimbursement paid to the pharmacy by the client and/or member may be based at least in part on the type of pharmacy network in which the pharmacy is included. Other factors may be used to determine the reimbursement amount in addition to the type of pharmacy network.

The wholesaler device 108 may be operated by a drug wholesaler, or an entity that is at least partially responsible buying drugs from a drug manufacturer and/or for selling drugs to pharmacies. Either or both of the pharmacy device 102 and benefit manager device 106 may be in communication with the wholesaler device 108 via network 104.

After a pharmacy has submitted a claim to a PBM for adjudication and fills the patient's prescription, the pharmacy purchases additional drugs from a drug wholesaler to refill its depleted stock. However, patients, doctors and/or pharmacies may attempt to abuse the system. For example, a pharmacy may submit claims to the PBM for adjudication of and payment for prescriptions which the pharmacy did not fill.

The purchase validation device 110, which may be operated by a PBM or a third party responsible for verifying certain claims submitted for adjudication, may therefore be in communication with benefit manager device 106, wholesaler device 108 and/or pharmacy device 102 over the network 104. The purchase validation device 110 may a part of the benefit manager device 106, or a separate device therefrom. The purchase validation device 110, the benefit manager device 106, the wholesaler device 108, and the pharmacy device 102 may each be electronic device and/or a computer system which include at least one processor.

The purchase validation device 110 may be in communication directly (e.g., through local storage) and/or through the network 104 (e.g., in a cloud configuration or software as a service) with a database 112. The database 112 may store pharmacy claims data 114, pharmacy data 116 and drug wholesaler data 118.

The pharmacy claims data 114 includes data relating to claims adjudicated by the PBM including monies paid to pharmacies as a result. The pharmacy claims data 114 generally reflects multiple adjudicated claims that were submitted by the pharmacy for adjudication during a period of time. A claim may be associated with a single prescription drug or multiple prescription drugs. The pharmacy data 116 includes data received from pharmacies, such as lists of drug wholesalers from which the pharmacies purchase drugs. The drug wholesaler data 118 includes data received from a drug wholesaler regarding specific quantities of drugs sold to a pharmacy.

While the system 100 in FIG. 1 is shown to include single devices 102, 106, 108, 110, 112, multiple devices may be involved. Such devices may be of the same type, or of different types. Network 104 may be multiple networks, which may communicate in series with each other or in parallel with one another and the devices in system 100.

Figure 2:
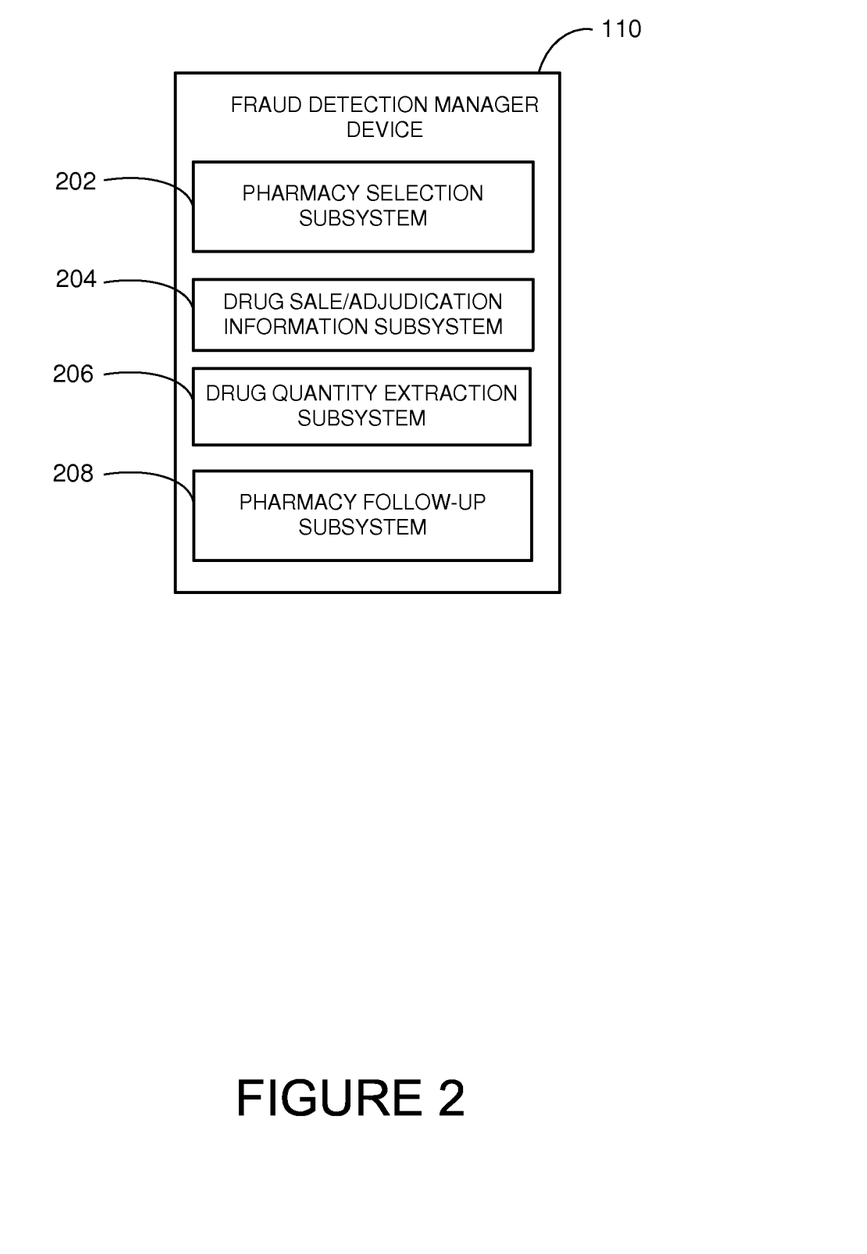
FIG. 2 is a block diagram of an example purchase validation device, according to an example embodiment.

FIG. 2 illustrates a block diagram of an example purchase validation device 110 according to an example embodiment. The purchase validation device 110 may include a pharmacy selection subsystem 202, a drug sale and adjudication information subsystem 204, a drug quantity extraction subsystem 206, and a pharmacy follow-up subsystem 208.

In general operation, the pharmacy selection subsystem 202 may flag pharmacies that have an elevated probability of being involved in fraudulent activity. A pharmacy which submits a high percentage of claims for drugs with high reimbursement amounts may be flagged, as may pharmacies which submit a high percentage of claims for drugs which are commonly abused.

The drug sale and adjudication information subsystem 204 requests and collects drug purchase information from a pharmacy and drug wholesaler, and aggregating claim adjudication data for the flagged pharmacies. Such drug purchase information may include the number and types of pharmaceuticals purchased by a pharmacy from a drug wholesaler, as well as the number and types of pharmaceuticals associated with claims submitted for adjudication by the pharmacy. This may include the number of units of a prescription drug by dosage, drug type, capsule type, method of administration, and the like, and may be indicated by National Drug Code (NDC).

The drug quantity extraction system 206 determines the number and type of drugs sold to the pharmacy based on the drug purchase information, and for determining the number and type of drugs associated with the claims submitted for adjudication by the pharmacy based on the pharmacy claims data. Such numbers may also be harmonized to account for different counting conventions among drug wholesalers, pharmacies, and PBMs. The drug quantity extraction subsystem 206 may analyzing the number of drug doses purchased by the pharmacy and submitted to the PBM for adjudication by the pharmacy to determine if there are any discrepancies.

Figure 3:
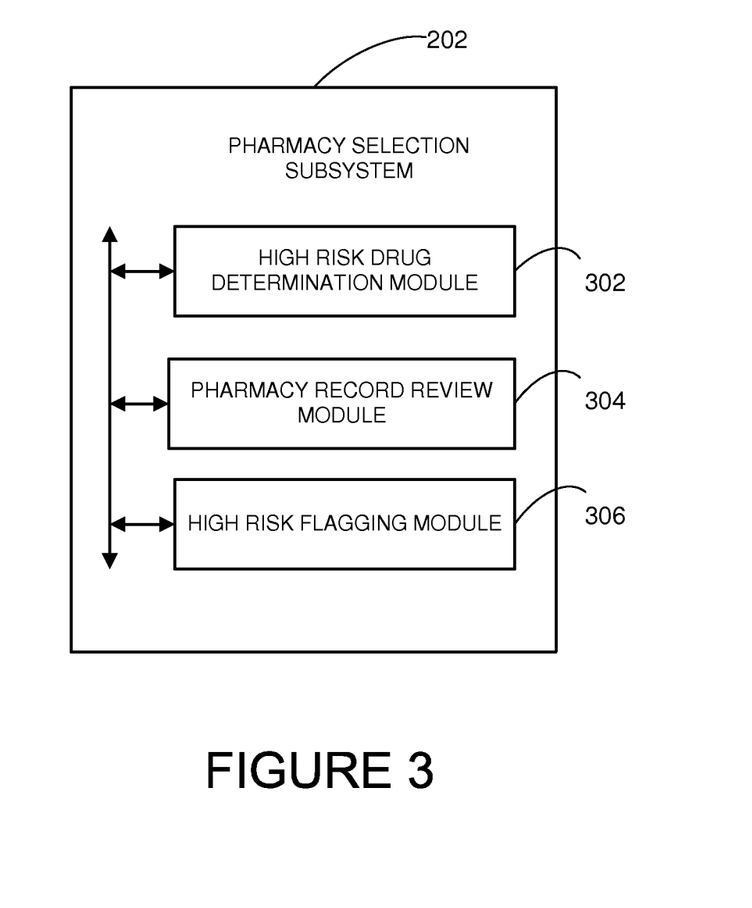
FIG. 3 is a block diagram of an example pharmacy selection subsystem, according to an example embodiment.

FIG. 3 illustrates an example pharmacy selection subsystem 202 that may be deployed in the purchase validation device 110, the benefit manager device 106, or otherwise deployed in another system. One or more modules are communicatively coupled and included in the pharmacy selection subsystem 202 to enable a pharmacy to be selected for purchase verification. The modules of the pharmacy selection subsystem 202 that may be included are a high risk drug determination module 302, a pharmacy record access and review module 304 and a high risk pharmacy flagging module 306. Other modules may also be included.

In some embodiments, the modules of the pharmacy selection subsystem 202 may be distributed so that some of the modules are deployed in the benefit manager device 106 and some are deployed in the purchase validation device 110. In one embodiment, the modules are deployed in memory and executed by a processor coupled to the memory. The functionality contained within modules 302-306 may be combined into a lesser number of modules, further divided among a greater number of modules, or redistributed among existing modules. Other configurations including the functionality of the modules may be used.

High risk drug determination module 302 may first determine which drugs, if any, are the most likely to be exploited via fraud. For example, drugs which provide pharmacies with a high reimbursement rate upon adjudication are often targets for pharmacies attempting to commit fraud. Submitting relatively few false claims for adjudication can result in sizeable payments from the PBM to the pharmacy. Similarly, drugs which are in high demand (such as pain medications, HGH, etc.) may also be flagged as high risk drugs by high risk drug determination module 302, as large numbers of these prescriptions could signal that a patient and/or doctor and/or pharmacy are operating a so-called "pill mill." Further criteria may include low reversal rates, higher than industry or geographical average sales, etc. The selection of high risk drugs may be automatic, or may be made manually input (e.g., by a device operator).

Pharmacy record review module 304 then accesses and reviews pharmacy adjudication records, such as those stored as the pharmacy claims data 114 and/or the pharmacy data 116, stored in the database 112. Claim adjudications involving high risk drugs are selected for evaluation and analysis. The high risk flagging module 306 then calculates whether the numbers of such selected claims are higher than a predetermined threshold. Where a pharmacy's high risk drug claim adjudications are below the predetermined threshold, no action is taken. However, where the pharmacy's high risk drug claim adjudications surpass the threshold, the high risk flagging module 306 identifies or flags the pharmacy for verification of the claims it submitted for adjudication.

Figure 4:
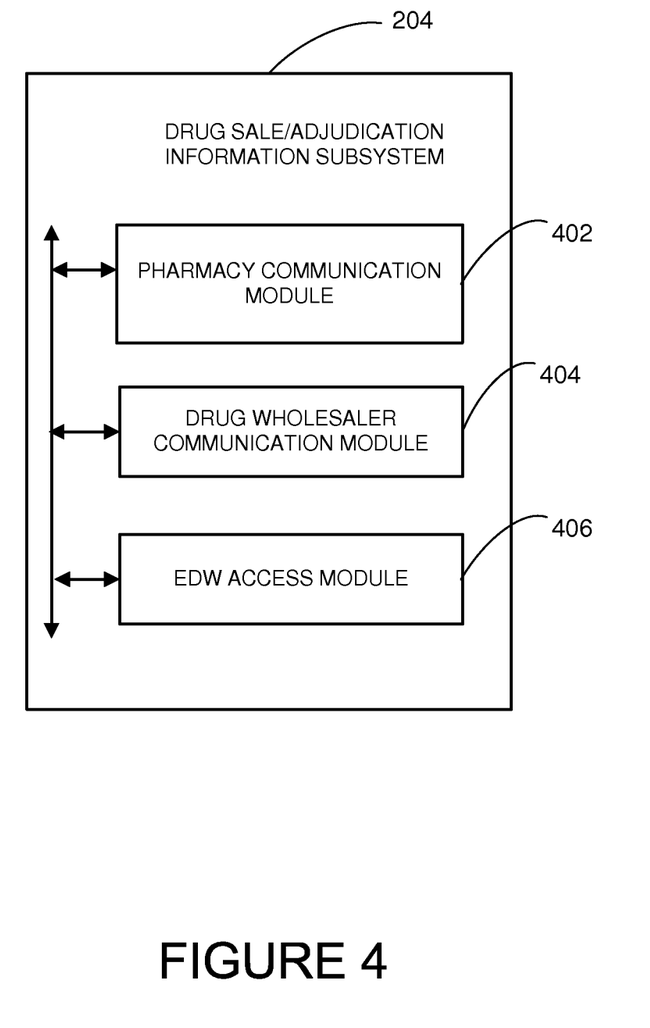
FIG. 4 is a block diagram of an example drug sale and adjudication information subsystem, according to an example embodiment.

FIG. 4 illustrates a block diagram of an example drug sale and adjudication information subsystem 204 according to an example embodiment, which may be deployed in the purchase validation device 110, the benefit manager device 106, or otherwise deployed in another system. One or more modules are communicatively coupled and included in the drug sale and adjudication information subsystem 204 to enable data to be collected regarding drug sales and claims submitted for adjudication. Drug sale and adjudication information subsystem 204 may include a pharmacy communication module 402, a drug wholesaler communication module 404, and a data access module 406. Other modules may also be included In some embodiments, the modules of the drug sale and adjudication information subsystem 204 may be distributed so that some of the modules are deployed in the benefit manager device 106 and some are deployed in the purchase validation device 110. In one embodiment, the modules are deployed in memory and executed by a processor coupled to the memory. The functionality contained within modules 402-406 may be combined into a lesser number of modules, further divided among a greater number of modules, or redistributed among existing modules. Other configurations including the functionality of the modules may be used.

The pharmacy communication module 402 may initiate communication with the pharmacy device 102 associated with a flagged pharmacy, either via email (such as through network 104), fax, or the like. The pharmacy communication module 402 may request that the pharmacy device instruct the pharmacy's drug wholesaler to transmit the drug wholesaler data 118 (which may include drug sale data) to the PBM regarding drugs sold by the drug wholesaler to the pharmacy during a period of time. Drug sale data may include invoice data and/or information relating to the number and type of unit of prescription drug sold. The drug wholesaler communication module 404 may then communicate with the wholesaler device 108, and receive drug wholesaler data therefrom. In some embodiments, the pharmacy device 102 may simply identify to the pharmacy communication module 404 the pharmacy's drug wholesaler. The drug wholesaler communication module 404 may then initiate communication with the wholesaler device 108 to receive the drug wholesaler data 118. The received drug wholesaler data 118 is stored in database 112. In some embodiments, pharmacies generally agree ahead of time to such audit procedures when signing on to be a part of a pharmacy network of a PBM.

The data access module 406 then accesses the drug wholesaler data 118 and the drug sale data therein, as well as the pharmacy claims data 114 from the database 112 to retrieve claim adjudication data submitted by the flagged pharmacy over the selected period of time.

Figure 5:
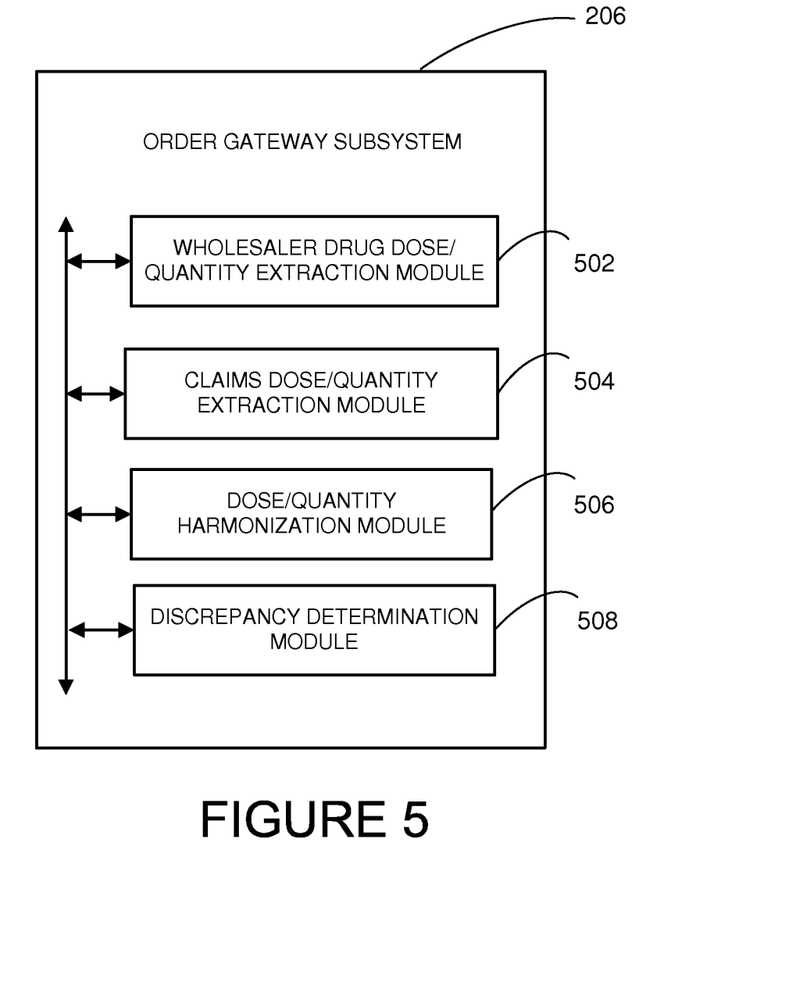
FIG. 5 is a block diagram of an example drug quantity extraction subsystem, according to an example embodiment.

FIG. 5 illustrates an example drug quantity extraction subsystem 206 according to an example embodiment, which may be deployed in the purchase validation device 110, the benefit manager device 106, or otherwise deployed in another system. One or more modules are communicatively coupled and included in the drug quantity extraction subsystem 206 to enable the determination of units of a prescription drugs sold to and submitted for adjudication by a pharmacy. Drug quantity extraction subsystem 206 may include a wholesaler drug unit extraction module 502, a claims drug unit extraction module 504, a drug unit harmonization module 506, and a discrepancy determination module 508. Other modules may also be included In some embodiments, the modules of the drug quantity extraction subsystem 206 may be distributed so that some of the modules are deployed in the benefit manager device 106 and some are deployed in the purchase validation device 110. In one embodiment, the modules are deployed in memory and executed by a processor coupled to the memory. The functionality contained within modules 502-508 may be combined into a lesser number of modules, further divided among a greater number of modules, or redistributed among existing modules. Other configurations including the functionality of the modules may be used.

Wholesaler drug unit extraction module 502 parses the accessed drug wholesaler data 118, and determines and/or extracts data regarding units of a prescription drug sold to the pharmacy therefrom. Indeed, the wholesaler devices 108 may merely transmit electronic copies of invoices and/or spreadsheets of data which are not standardized. Such documents may require the wholesaler drug unit extraction module 502 to perform optical character recognition (OCR) thereon to extract the data regarding units of a prescription drug sold to the pharmacy contained therein. In some embodiments, the wholesaler drug unit extraction module 502 may extract data regarding units of a prescription drug sold to the pharmacy from spreadsheets or other formatting of data received from the wholesaler devices 108.

The claims drug unit extraction module 504 determines and/or extracts data regarding units of a prescription drug submitted for adjudication by the pharmacy in the accessed pharmacy claims data 114. As discussed above, data regarding units of a prescription drug may include the quantity and type of drugs sold to pharmacies or submitted by the pharmacies to PBMs for adjudication, and may include a drug's National Drug Code (NDC), drug name, drug maker, quantity per prescription, capsule type, dosage, number of doses and the like. The NDC serves as a universal product identifier for human drugs. The FDA publishes the listed NDC numbers and information submitted as part of the listing information in the NDC Directory. For a PBM service performing a purchase validation, the NDC identifier number may identify the same products when purchased from one or more different wholesalers.

Different drug wholesalers and PBMs may have different drug unit numbering conventions. For example, birth control pills are generally sold in three-packs of thirty pills each, which may be considered: a single unit, three units, or ninety individual doses, depending on the entity classifying the drug sale/adjudication. The drug unit harmonization module 506 considers such varying reporting conventions, and harmonizes the data regarding units of a prescription drug from the drug wholesaler data 118 and the data regarding units of a prescription drug from the pharmacy claims data 114. Such harmonization creates a direct, one-to-one, drug-for-drug, pill-for-pill, dose-for-dose comparison between drugs purchased by the pharmacy and drug claims reimbursed by the PBM.

The discrepancy determination module 508 then compares the number of units of a prescription drug submitted for adjudication by the pharmacy with the number of units of a prescription drug sold to the pharmacy by the drug wholesaler. Where the pharmacy has requested adjudication for more of a given drug than it has actually purchased by a threshold amount, the discrepancy determination module 508 detects that fraud may have occurred.

Figure 6:
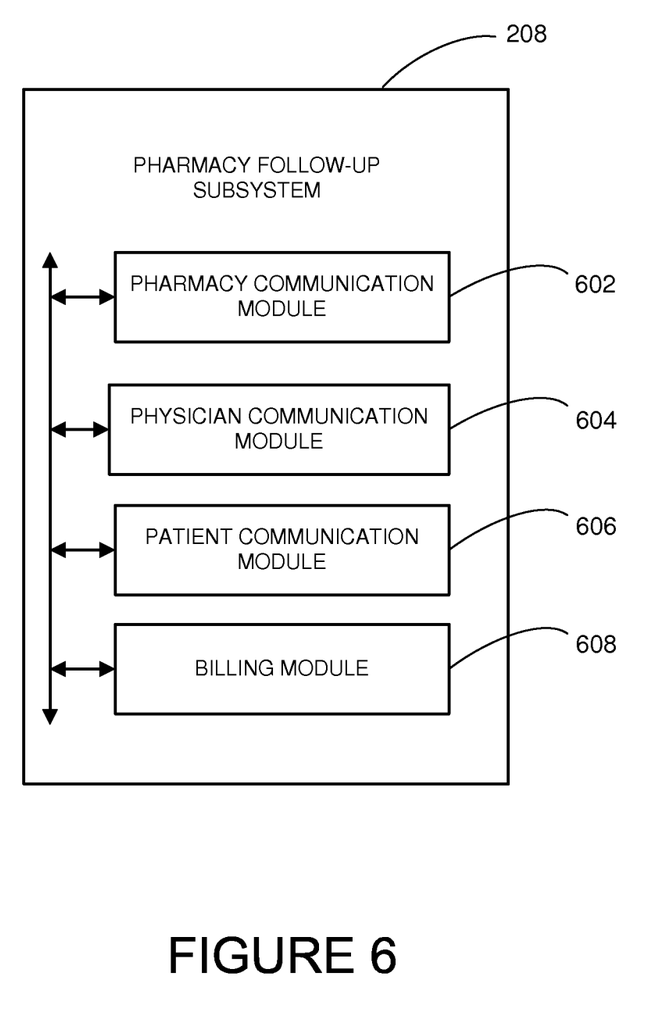
FIG. 6 is a block diagram of an example pharmacy follow-up subsystem.

FIG. 6 illustrates an example pharmacy follow-up subsystem 208 according to an example embodiment, which may be deployed in the purchase validation device 110, the benefit manager device 106, or otherwise deployed in another system. One or more modules are communicatively coupled and included in the pharmacy follow-up subsystem 208 to enable further investigation of any discrepancies found. The pharmacy follow-up subsystem 208 may include a pharmacy communication module 602, a physician communication module 604, a patient communication module 606, and a billing module 608. Other modules may also be included In some embodiments, the modules of the pharmacy follow-up subsystem 208 may be distributed so that some of the modules are deployed in the benefit manager device 106 and some are deployed in the purchase validation device 110. In one embodiment, the modules are deployed in memory and executed by a processor coupled to the memory. The functionality contained within modules 602-608 may be combined into a lesser number of modules, further divided among a greater number of modules, or redistributed among existing modules. Other configurations including the functionality of the modules may be used.

The pharmacy communication module 602 may transmit to the pharmacy device 102 a request for additional explanation—essentially, an explanation as any discrepancies between the units of a prescription drug submitted for adjudication and the number of units of a prescription drug purchased by the pharmacy. The request may be generated dynamically or automatically. To verify the claims submitted by the pharmacy for adjudication, the physician communication module 604 may transmit a request to the physician or other type of prescriber who wrote a prescription at issue (or to a prescriber device associated with the prescriber). The patient communication module 606 may do the same with a patient (or a patient device) whose prescription is at issue. Responses by a patient, physician, or the pharmacy may be received and reviewed electronically, or manually.

The billing module 608 may transmit to the pharmacy device 102 a bill for cost and reimbursement amounts associated with adjudicating drug claims above the number of units of a prescription drug purchased by the pharmacy. The bill (or pharmacy reimbursement request) may be transmitted electronically, faxed, mailed, or otherwise provided to the pharmacy.

Figure 7:
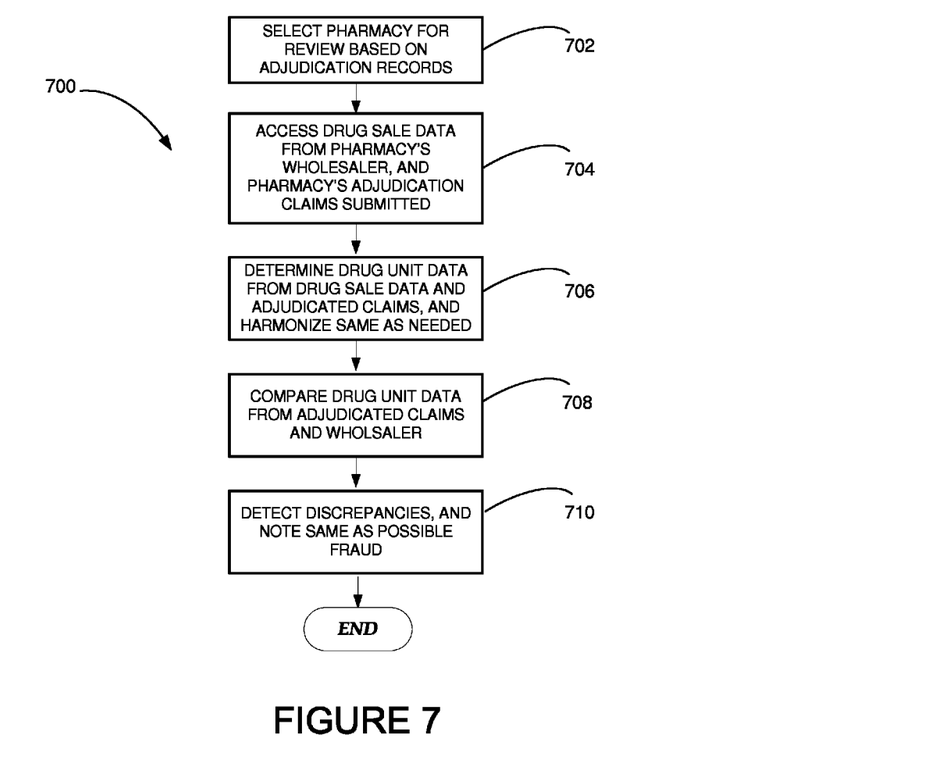
FIG. 7 is an example process flow illustrating a method for purchase verification of adjudicated claims, according to an example embodiment.

FIG. 7 illustrates a method 700 for purchase verification of adjudicated claims, according to an example embodiment. The method 700 may be performed by the purchase validation device 110, partially by the purchase validation device 110 and partially by the benefit manager device 106, or may be otherwise implemented.

At block 702, a pharmacy is selected for review based on its adjudication data. As discussed above, a pharmacy which submits higher than expected numbers of claims involving expensive drugs, high demand drugs, low reversal rates, etc. may be selected for review.

At block 704, the drug sale data from the pharmacy's wholesaler is accessed, along with the claims that were submitted by the pharmacy to the PBM for adjudication. The data from the pharmacy's wholesaler may have been received in the form of invoices, electronically via spreadsheet, or in another form. The data regarding claims submitted by the pharmacy to the PBM for adjudication may be stored in an accessible database by the PBM.

At block 706, data regarding the number of units of a prescription drug is determined based on the drug sale data and the adjudicated claims, and in some embodiments, is harmonized. The data regarding the number of units of a prescription drug may be determined based on and/or extracted from the drug sale data and adjudicated pharmacy claims data. Harmonization of the various data regarding the number of units of a prescription drug may also be performed, considering the varying reporting conventions. Such harmonization creates a direct, one-to-one, drug-for-drug, pill-for-pill, dose-for-dose comparison between drugs purchased by the pharmacy and drug claims reimbursed by the PBM.

At block 708, the number of units of a prescription drug in the adjudicated claims is compared with the number of units of a prescription drug sold by the wholesaler. As the number of units of a prescription drug from the adjudicated claims represents the number, type, dose, etc. of the drugs reportedly dispensed by the pharmacy, while the number of units of a prescription drug sold by the wholsalers represents the number, type, dose, etc. of the drugs sold to the pharmacy, a comparison of such data can detect that a pharmacy submitted a claim (and received a reimbursement) for a drug which it never purchased. Thus, at block 710, discrepancies are detected and noted as possible fraud.

Figure 8:
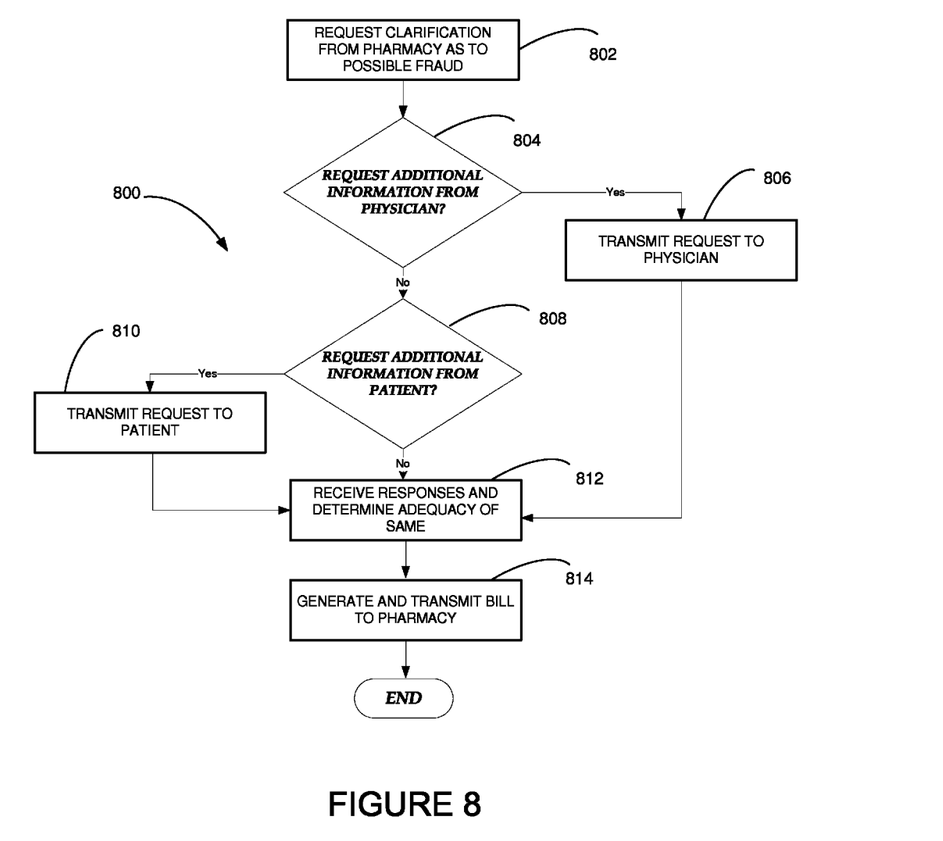
FIG. 8 is an example process flow illustrating a method for investigating possible fraud, according to an example embodiment.

FIG. 8 illustrates a method 800 for investigating possible fraud, according to an example embodiment. The method 800 may be performed by the purchase validation device 110, partially by the purchase validation device 110 and partially by the benefit manager device 106, or may be otherwise implemented.

At block 802, where a possible fraud has been detected, a request is transmitted to the pharmacy for clarification as to the seemingly fraudulent activity. The pharmacy may be asked to explain the detected discrepancies, and/or provide additional data to support the claims it submitted.

At block 804, a determination is made as to whether to transmit an additional information request to an associated physician. Such a physician may be able to confirm whether an adjudicated claim is legitimate, or was contrived by the pharmacy and/or patient. Where such a transmission is to be made, at block 806, the request for verification is transmitted to the physician (or physician device).

Similarly, at block 808, a determination is made as to whether to transmit an additional information request to an associated patient. Such a patient may be able to confirm whether an adjudicated claim is legitimate, or was contrived by the pharmacy and/or physician. Where such a transmission is to be made, at block 810, the request for verification is transmitted to the patient (or patient device).

At block 812, responses are received, and a determination is made as to whether the responses clarify the circumstances of the possible fraud as being legitimate. This step may be manual or computerized. Where a pharmacy provides additional wholesaler from which it bought drugs, any such additional drug purchases may be investigated via the purchase verification method above.

At block 814, where a possible fraud has been detected and has not been ruled out, a bill is generated and transmitted to the pharmacy requesting repayment of costs and reimbursement amounts associated with adjudicating the fraudulent claims.

Figure 9:
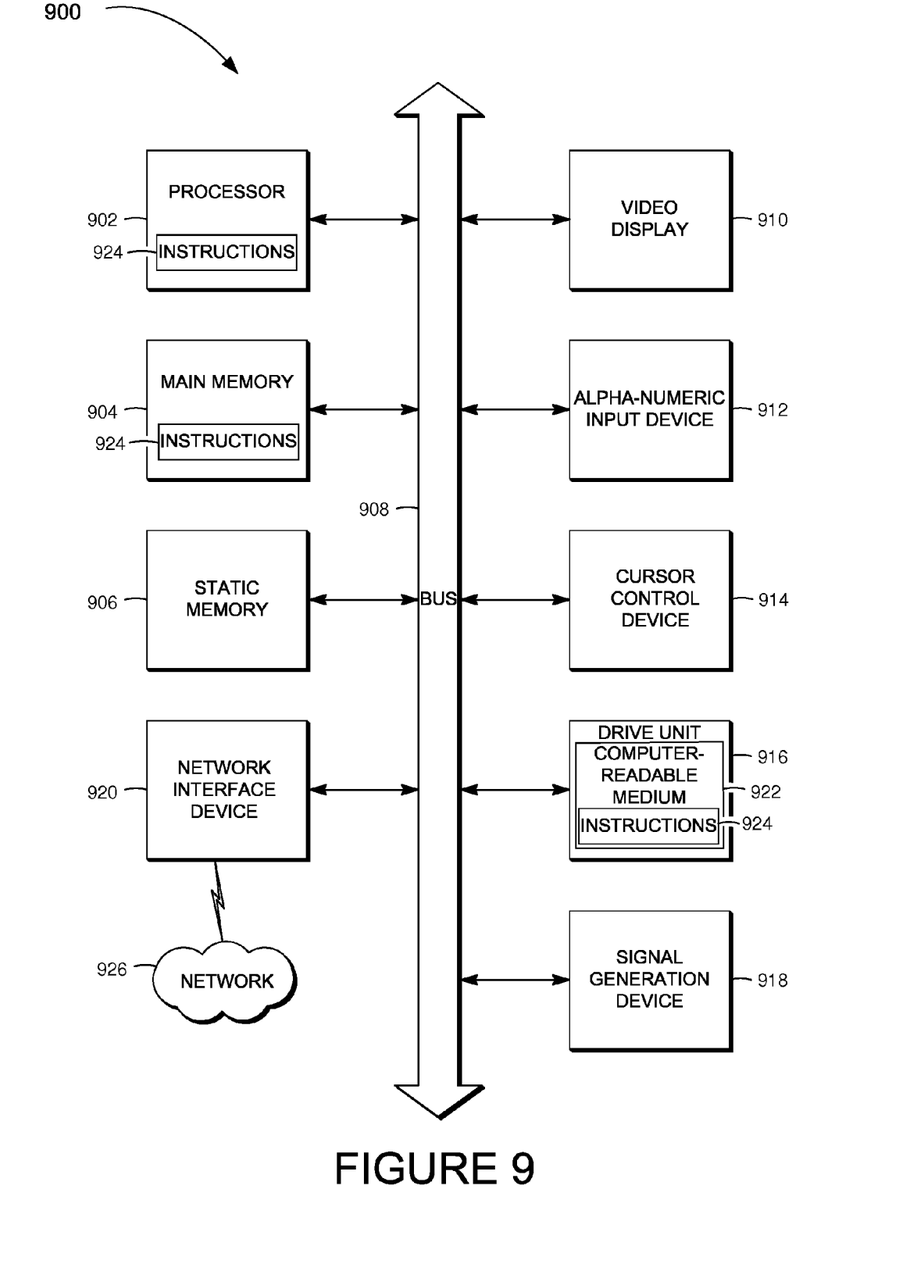
FIG. 9 is a block diagram of a machine in the example form of a computer system within which a set of instructions for causing the machine to perform any one or more of the methodologies discussed herein may be executed or stored.

FIG. 9 shows a block diagram of a machine in the example form of a computer system 900 within which a set of instructions may be executed causing the machine to perform any one or more of the methods, processes, operations, or methodologies discussed herein. The pharmacy device 102, the benefit manager device 106, the wholesaler device 108 and/or the purchase validation device 110 may include the functionality of one or more computer systems 900.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 900 includes a processor 902 (e.g., a central processing unit (CPU) a graphics processing unit (GPU) or both), a main memory 904 and a static memory 906, which communicate with each other via a bus 908. The computer system 900 further includes a video display unit 910 (e.g., a liquid crystal display (LCD) or a cathode ray tube (CRT)). The computer system 900 also includes an alphanumeric input device 912 (e.g., a keyboard), a cursor control device 914 (e.g., a mouse), a drive unit 916, a signal generation device 918 (e.g., a speaker) and a network interface device 920.

The drive unit 916 includes a computer-readable medium 922 on which is stored one or more sets of instructions (e.g., software 924) embodying any one or more of the methodologies or functions described herein. The software 924 may also reside, completely or at least partially, within the main memory 904 and/or within the processor 902 during execution thereof by the computer system 900, the main memory 904 and the processor 902 also constituting computer-readable media.

The software 924 may further be transmitted or received over a network 926 via the network interface device 920.

While the computer-readable medium 922 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, drug sale data is accessed from a prescription drug wholesaler regarding prescription drugs sold to the pharmacy by the prescription drug wholesaler during a period of time. A number of units of a prescription drug sold to the pharmacy are determined based on the drug sale data during the period of time. Pharmacy claims data over the period of time is accessed, where the pharmacy claims data reflects a plurality of adjudicated claims, and the plurality of adjudicated claims are a plurality of claims that were submitted for adjudication by the pharmacy during the period of time. A number of units of a prescription drug associated with the plurality of claims submitted during the period of time by the pharmacy for adjudication are determined based on the pharmacy claims data. The number of units of the prescription drug associated with the plurality of adjudicated claims that were submitted for adjudication by the pharmacy is compared with the number of units of the prescription drug sold to the pharmacy. A determination is then made as to whether a discrepancy exists based on the results of the comparison.

Thus, methods and systems for purchase verification have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The invention claimed is:

1. A method comprising:
accessing, on a processor, prescription drug wholesaler sale data regarding prescription drugs sold to a pharmacy by a prescription drug wholesaler during a retrospective time period;
determining, on the processor, a number of units of a prescription drug sold by the prescription drug wholesaler to the pharmacy based on the accessed prescription drug wholesaler sale data;
accessing, on the processor, adjudicated pharmacy claims data of the retrospective time period, the adjudicated pharmacy claims data reflecting a plurality of adjudicated claims, the plurality of adjudicated claims being a plurality of claims of the retrospective time period that were submitted on behalf of the pharmacy and adjudicated and dispensing approved by a benefit manager, the dispensing approved reflecting approval by the benefit manager of the plurality of claims for dispensing by the pharmacy;
determining, on the processor, a number of units of the prescription drug associated with the plurality of adjudicated claims;
comparing, on the processor, the number of units of the prescription drug associated with the plurality of adjudicated claims with the number of units of the prescription drug sold to the pharmacy; and
determining, on the processor, that a discrepancy exists based on a result of the comparison reflecting that the pharmacy has filled prescriptions for more prescription drugs than the pharmacy has purchased.

2. The method of claim 1, where determining that the discrepancy exists comprises:
determining that the discrepancy exists where the number of units of the prescription drug associated with the plurality of adjudicate claims that were submitted for adjudication by the pharmacy is greater than the number of units of the prescription drug sold to the pharmacy by a predetermined amount.

3. The method of claim 1, further comprising:
generating a pharmacy explanation request to request an explanation of the discrepancy from the pharmacy; and
transmitting the pharmacy explanation request to a pharmacy device, the pharmacy device being associated with the pharmacy.

4. The method of claim 1, further comprising:
determining an excess number of units of the prescription drug associated with the plurality of adjudicated claims that were submitted for adjudication by the pharmacy greater than the number of units of the prescription drug sold to the pharmacy;
generating a pharmacy reimbursement request for reimbursement of the excess number of units of the prescription drug.

5. The method of claim 1, further comprising:
identifying the pharmacy for adjudicated claims verification,
wherein access of the prescription drug wholesaler sale data is based on identification of the pharmacy.

6. The method of claim 1, where identification of the pharmacy comprises:
identifying a high risk drug;
accessing claims data submitted during a period of time for the high risk drug by the pharmacy;
determining a number of adjudicated claims relating to the high risk drug during the period of time based on the claims data; and
selecting the pharmacy for verification where the number claims submitted by the pharmacy relating to the high risk drug is greater than a verification criterion.

7. The method of claim 6, where the verification criterion is a determined amount of adjudicated claims associated with the high risk drug.

8. The method of claim 1, wherein determining the number of units of a prescription drug sold to the pharmacy includes recognizing units of the prescription drug in the drug sale data.

9. The method of claim 1, wherein determining the number of units of a prescription drug associated with claims submitted by the pharmacy for adjudication includes recognizing units of the prescription drug in the plurality of adjudicated claims.

10. The method of claim 1, further comprising:
harmonizing the number of units of the prescription drug sold to the pharmacy with the number of unit of the prescription drug submitted by the pharmacy for adjudication such that the number of doses, dosage and capsule type in each agree.

11. The method of claim 1, further comprising:
identifying the prescription drug wholesaler that sell drugs to the pharmacy; and
transmitting a drug sale data request to a prescription drug wholesaler device associated with the prescription drug wholesaler.

12. The method of claim 1, further comprising:
generating a physician verification request for requesting verification of a claim from a physician; and
transmitting the physician verification request to a physician device, the physician device being associated with a physician.

13. The method of claim 1, further comprising:
generating a patient verification request for requesting verification of a claim from a patient; and
transmitting the patient verification request to a patient device, the patient device being associated with a patient.

14. The method of claim 1, where drug sale data includes invoice data relating to sales of drugs from a drug wholesaler to the pharmacy.

15. The method of claim 1, wherein the prescription drug is a narcotic.

16. The method of claim 1, wherein the plurality of adjudicated claims includes a drug claim for filling of the prescription drug on behalf of a patient that is not in accordance with a prescription,
wherein the discrepancy is based on the results of the comparison and that the plurality of adjudicated claims includes the drug claim that is not in accordance with the prescription.

17. The method of claim 1, wherein adjudication by the benefit manager includes eligibility verification, co-pay determination, and drug utilization review.

18. The method of claim 1, wherein the prescription drug wholesaler purchased the prescription drug from a drug manufacturer of the prescription drug and sold the prescription drug to the pharmacy.

19. The method of claim 1, wherein the retrospective time period reflects a sufficient period of time over which an audit of the number of units of the prescription drug associated with the plurality of adjudicated claims and the number of units of the prescription drug sold to the pharmacy can be conducted.

20. The method of claim 1, wherein the prescription drug wholesaler sale data includes data received from a drug wholesaler in response to an inquiry regarding specific quantities of the prescription drug sold to the pharmacy.

21. A non-transitory machine-readable medium comprising instructions, which when executed by one or more processors, cause the one or more processors to perform the following operations:
- access prescription drug wholesaler sale data regarding prescription drugs sold to a pharmacy by a prescription drug wholesaler during a retrospective time period;
- determine a number of units of a prescription drug sold by the prescription drug wholesaler to the pharmacy based on the accessed prescription drug wholesaler sale data;
- access adjudicated pharmacy claims data of the retrospective time period, the adjudicated pharmacy claims data reflecting a plurality of adjudicated claims, the plurality of adjudicated claims being a plurality of claims of the retrospective time period that were submitted on behalf of the pharmacy and adjudicated and dispensing approved by a benefit manager, the dispensing approved reflecting approval by the benefit manager of the plurality of claims for dispensing by the pharmacy;
- determine a number of units of the prescription drug associated with the plurality of adjudicated claims;
- compare the number of units of the prescription drug associated with the plurality of adjudicated claims with the number of units of the prescription drug sold to the pharmacy; and
- determine that a discrepancy exists based on a result of the comparison reflecting that the pharmacy has filled prescriptions for more prescription drugs than the pharmacy has purchased.

22. A system comprising:
- a processor and a memory coupled to the processor;
- a data access module deployed in the memory and executed by the processor to access prescription drug wholesaler sale data regarding prescription drugs sold to a pharmacy by a prescription drug wholesaler during a retrospective time period, and adjudicated pharmacy claims data of the retrospective time period, the adjudicated pharmacy claims being a plurality of adjudicated claims, the plurality of adjudicated claims being a plurality of claims of the retrospective time period that were submitted on behalf of the pharmacy and adjudicated and dispensing approved by a benefit manager, the dispensing approved reflecting approval by the benefit manager of the plurality of claims for dispensing by the pharmacy; and
- a drug quantity extraction module deployed in the memory and executed by the processor to determine a number of units of a prescription drug sold by the prescription drug wholesaler to the pharmacy based on the accessed prescription drug wholesaler sale data, and a number of units of the prescription drug associated with the plurality of adjudicated claims;
- wherein the drug quantity extraction module compares the number of units of the prescription drug associated with the plurality of adjudicated claims with the number of units of the prescription drug sold to the pharmacy, and determines that a discrepancy exists based on a result of the comparison reflecting that the pharmacy has filled prescriptions for more prescription drugs than the pharmacy has purchased.

\* \* \* \* \*